United States Patent
Nakamura et al.

(10) Patent No.: US 10,806,149 B2
(45) Date of Patent: Oct. 20, 2020

(54) METHOD FOR PRODUCING SILVER-ION ANTIBACTERIAL LIQUID, SILVER-ION ANTIBACTERIAL LIQUID PRODUCED BY SAID METHOD, METHOD FOR PRODUCING SILVER-ION ANTIBACTERIAL POWDER, AND SILVER-ION ANTIBACTERIAL POWDER PRODUCED BY SAID METHOD

(75) Inventors: Kenji Nakamura, Osaka (JP); Koji Nakamura, Osaka (JP)

(73) Assignee: Taiki Corp., Ltd., Osaka (JP)

( * ) Notice: Subject to any disclaimer, the term of this patent is extended or adjusted under 35 U.S.C. 154(b) by 0 days.

(21) Appl. No.: 14/342,210

(22) PCT Filed: Aug. 31, 2012

(86) PCT No.: PCT/JP2012/072208
§ 371 (c)(1),
(2), (4) Date: Jul. 15, 2014

(87) PCT Pub. No.: WO2013/031964
PCT Pub. Date: Mar. 7, 2013

(65) Prior Publication Data
US 2014/0329899 A1 Nov. 6, 2014

(30) Foreign Application Priority Data
Sep. 1, 2011 (JP) .................. 2011-191039

(51) Int. Cl.
*A01N 59/16* (2006.01)
*A61Q 19/00* (2006.01)
(Continued)

(52) U.S. Cl.
CPC ............. *A01N 59/16* (2013.01); *A01N 25/02* (2013.01); *A01N 25/12* (2013.01); *A61K 8/19* (2013.01);
(Continued)

(58) Field of Classification Search
CPC ........ A01N 59/16; A01N 25/12; A01N 37/36; A01N 25/02; A61K 8/19; A61K 8/26;
(Continued)

(56) References Cited

U.S. PATENT DOCUMENTS 1,782,353 A * 11/1930 Jaeger .................... C01B 33/46
502/234
2002/0123523 A1 9/2002 Arata
2008/0292673 A1 11/2008 Crudden

FOREIGN PATENT DOCUMENTS

CN 101742915 A 6/2010
JP 63-265809 A 11/1988
(Continued)

OTHER PUBLICATIONS

Pifferi et el. Stabilityof Glucose Oxidase and Catalase Adsorbed on Variously Activated 13X Zeolite; Biotechnology and Bioengineering, vol. XXIV, pp. 2155-2165, 1982.*
(Continued)

*Primary Examiner* — Isis A Ghali
(74) *Attorney, Agent, or Firm* — Knobbe Martens Olson & Bear LLP

(57) ABSTRACT

A method for producing silver-ion antibacterial liquid using a type A or type X silver zeolite includes a process to weigh silver zeolite for obtain its blending quantity in a range of 0.1 to 20.0 percent by weight and to weigh citric acid for obtaining its blending quantity such that its blending ratio to the silver zeolite becomes 1.2 or greater, followed by blending of the two into purified water; a process to mix under agitation the silver zeolite and citric acid blended in the purified water to prepare a mixture liquid containing at least a citric acid-silver complex and silica hydrate; and a process to remove the silica hydrate produced in the mixture liquid. The production method can produce at low cost a
(Continued)

silver-ion antibacterial liquid offering immediate bactericidal effect.

2 Claims, 5 Drawing Sheets

(51) Int. Cl.
| | | |
|---|---|---|
| *A61K 8/26* | (2006.01) | |
| *A61Q 15/00* | (2006.01) | |
| *A61K 8/19* | (2006.01) | |
| *A01N 25/02* | (2006.01) | |
| *A01N 25/12* | (2006.01) | |
| *B01D 21/00* | (2006.01) | |

(52) U.S. Cl.
CPC ............... *A61K 8/26* (2013.01); *A61Q 15/00* (2013.01); *A61Q 19/00* (2013.01); *A61K 2800/56* (2013.01); *B01D 21/00* (2013.01)

(58) Field of Classification Search
CPC .... A61K 2800/56; A61Q 15/00; A61Q 19/00; B01D 21/00
See application file for complete search history.

(56) References Cited

FOREIGN PATENT DOCUMENTS

| JP | 08-092051 A | 4/1996 |
|---|---|---|
| JP | 2000-247822 A | 9/2000 |
| JP | 2001-519361 A | 10/2001 |
| JP | 2002-068914 A | 3/2002 |
| JP | 2007-210931 A | 8/2007 |
| JP | 2008-081739 A | 4/2008 |
| JP | 2012-072134 A | 4/2012 |
| WO | WO 1999/065317 A1 | 12/1999 |
| WO | WO 2008/144015 A2 | 11/2008 |
| WO | WO 2010/003627 A1 | 1/2010 |
| WO | WO 2010/145922 A2 | 12/2010 |

OTHER PUBLICATIONS

Noboru Aoki, "Jintai Jozai Kin no Hanashi (A Story of Indigenous Bacteria in Human Body)," Noboru Aoki, Shueisha Shinsho, pp. 182-183, Dec. 20, 2009 (ninth reprint).

http://www.texasnaturalsupply.com/Tinosan-SDC-Natural-Preservative-p/tsnp-pv.htm, by Texas Natural Supply, accessed Feb. 13, 2014.

International Search Report issued by Japan Patent Office dated Dec. 4, 2012 in the corresponding PCT patent application No. PCT/JP2012/072208.

Stogian Djokić,"Synthesis and Antimicrobial Activity of Silver Citrate Complexes," Bioinorganic Chemistry and Applications, vol. 47, No. 6, Jan. 1, 2008—8 pages.

The extended European search report issued by European Patent Office dated Feb. 6, 2015 in the corresponding European patent application No. 12828294.4—8 pages.

The Second Office Action issued by The State Intellectual Property Office of People's Republic of China dated Aug. 13, 2015 (with a machine translation thereof) in the corresponding Chinese patent application No. 201280046843.4—10 pages.

Sivler citrate, https://www.chemicalbook.com/ChemicalProductProperty_EN_CB8425982.htm, accessed on May 27, 2019.

* cited by examiner

[Fig. 1]
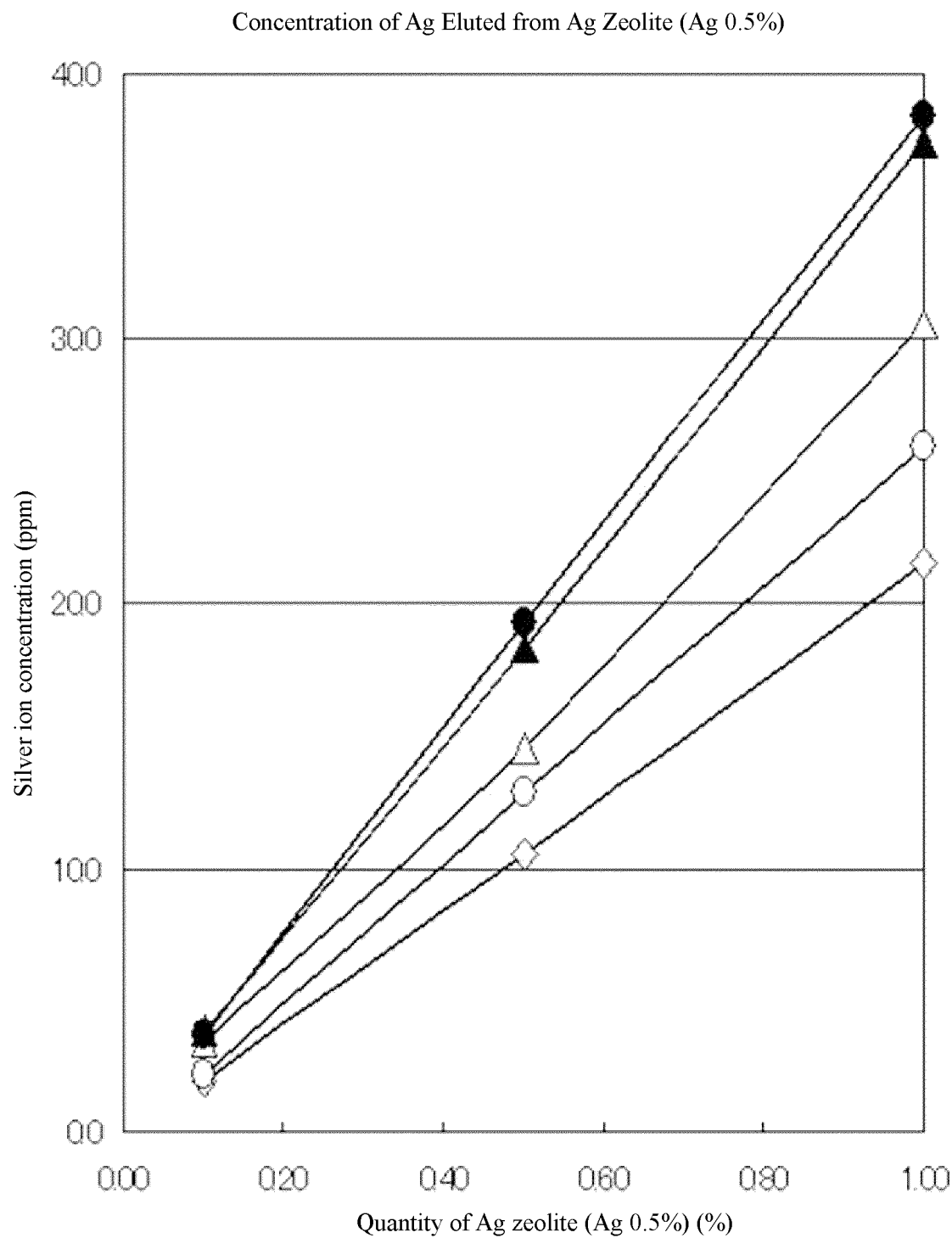

[Fig. 2]
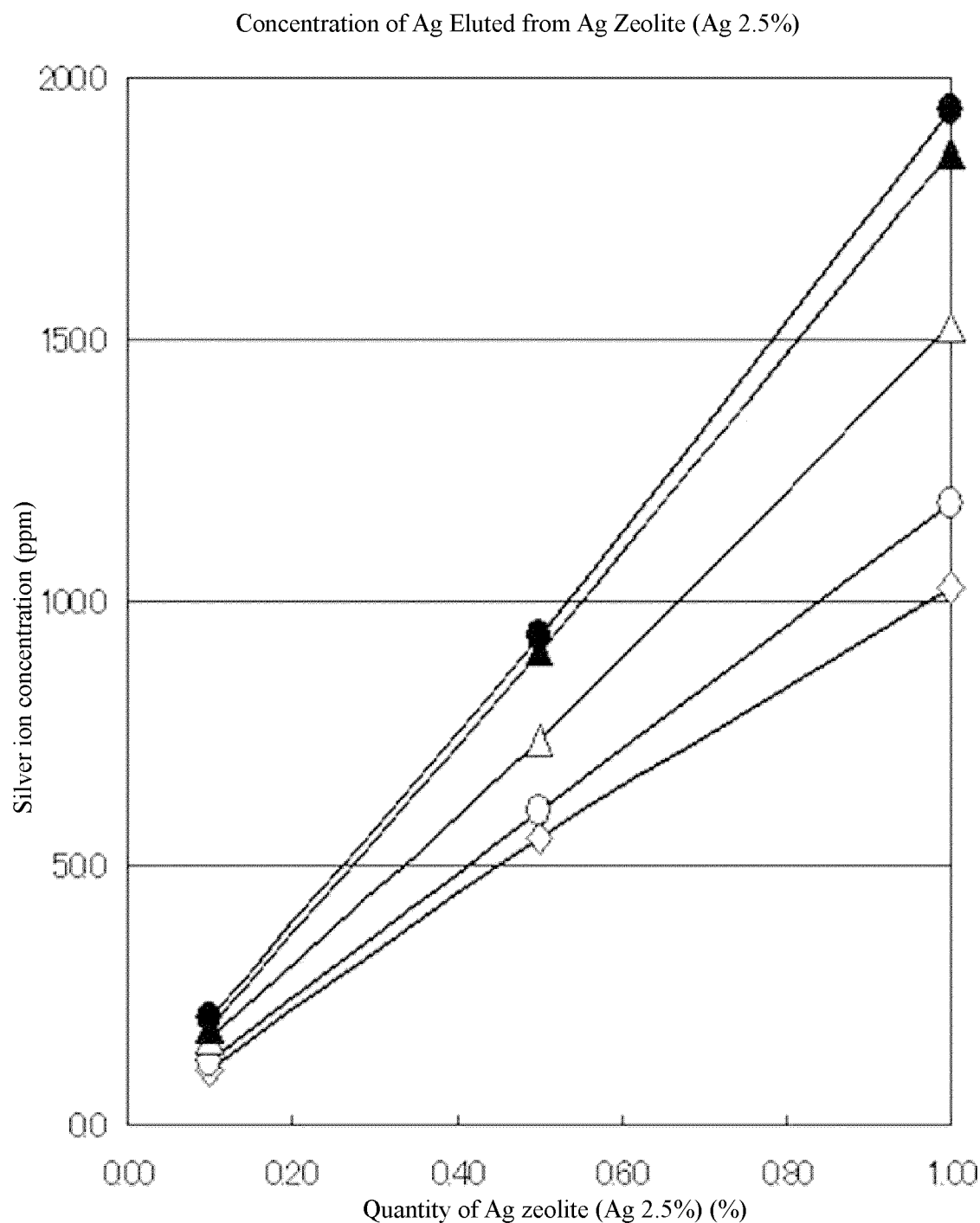

[Fig. 3]
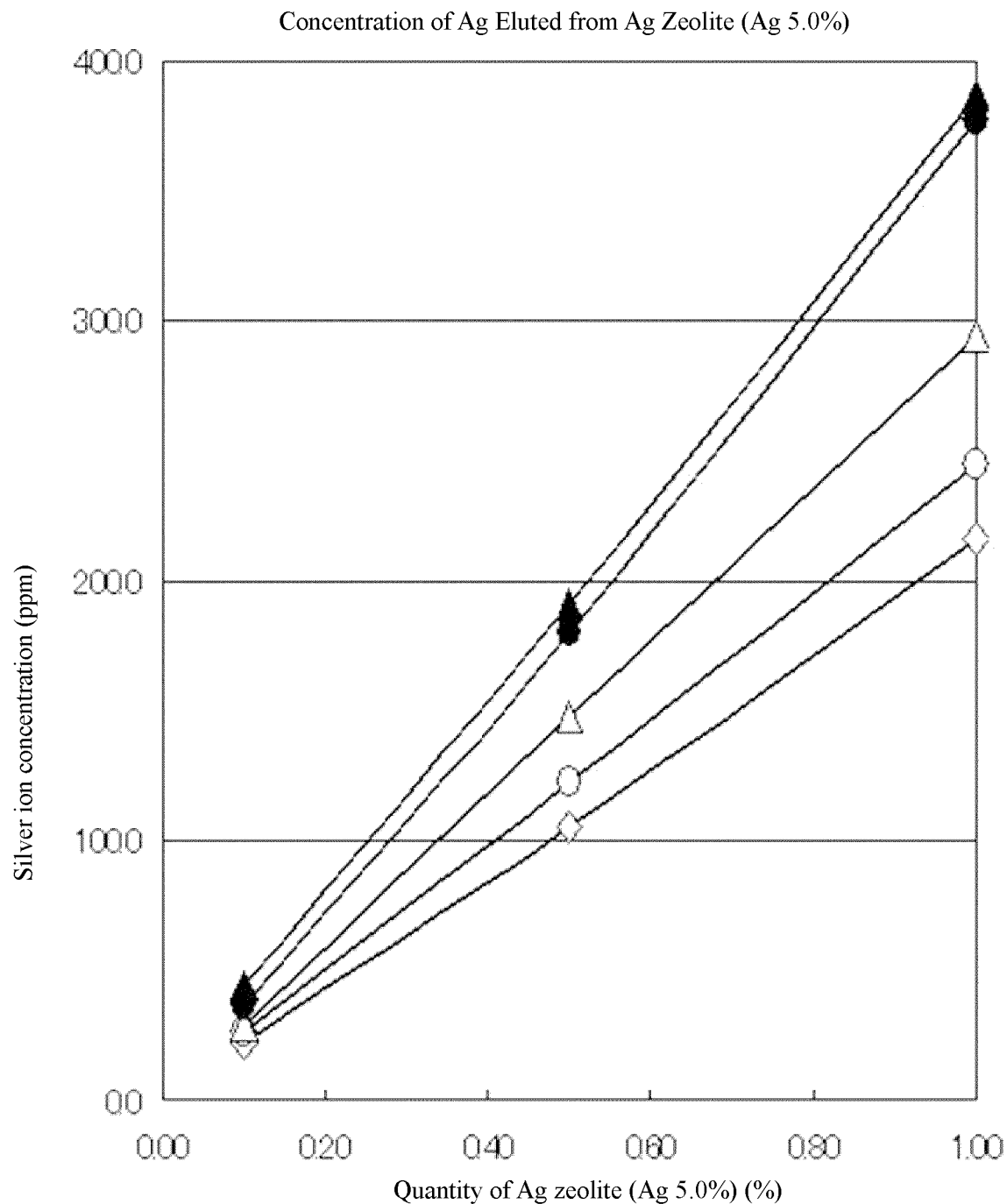

[Fig. 4]
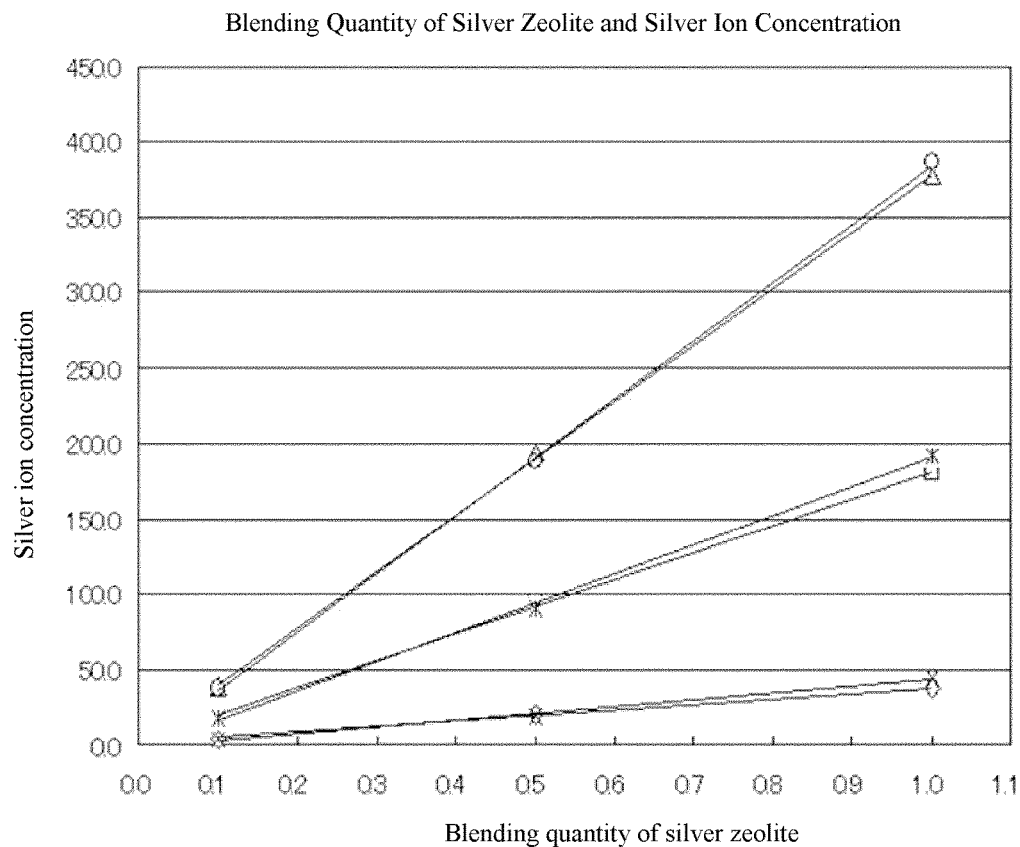
[Fig. 5]

[Fig. 6]
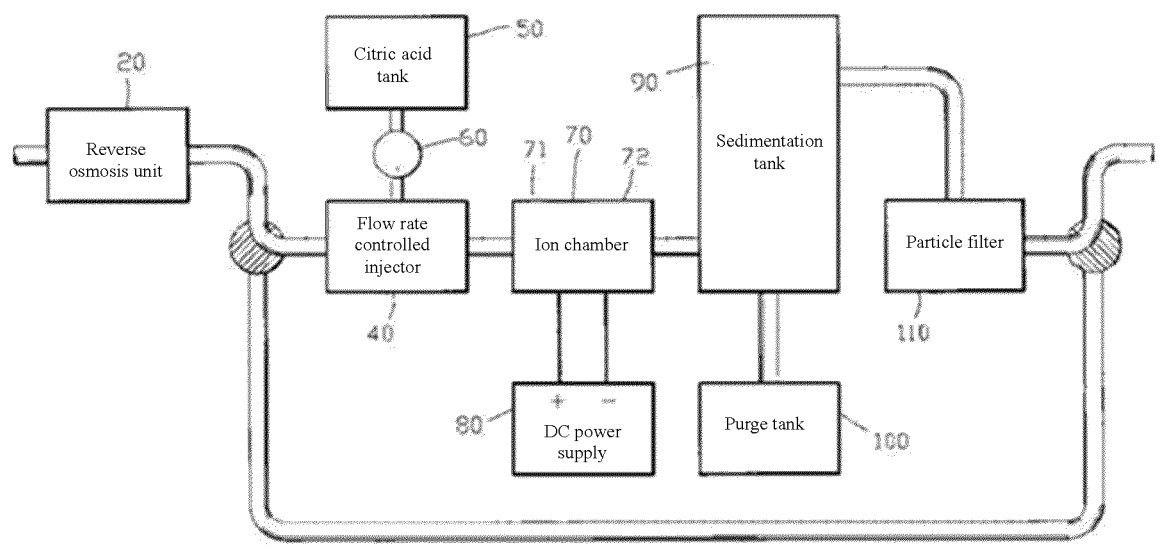

METHOD FOR PRODUCING SILVER-ION ANTIBACTERIAL LIQUID, SILVER-ION ANTIBACTERIAL LIQUID PRODUCED BY SAID METHOD, METHOD FOR PRODUCING SILVER-ION ANTIBACTERIAL POWDER, AND SILVER-ION ANTIBACTERIAL POWDER PRODUCED BY SAID METHOD

This application is the U.S. National Phase under 35 U.S.C. § 371 of International Application PCT/JP2012/072208, filed Aug. 31, 2012, which claims priority to Japanese Patent Application No. 2011-191039, filed Sep. 1, 2011. The International Application was published under PCT Article 21(2) in a language other than English.

TECHNICAL FIELD

The present invention relates to a method for producing silver-ion antibacterial liquid that involves using a silver zeolite as highly safe, low-cost material and eluting silver ions contained in its crystal structure, as well as a silver-ion antibacterial liquid produced by such method, and a method for producing silver-ion antibacterial powder as well as a silver-ion antibacterial powder produced by such method.

BACKGROUND ART

Bacteria are said to produce odor by breaking down human secretions. For example, the cause of underarm odor is the sweat secreted from the apocrine sweat glands in the skin; specifically when this sweat is secreted onto the skin, it is mixed with the fat secreted from the sebaceous glands and sweat secreted from the eccrine sweat glands, and as the resulting mixture is broken down by the indigenous bacteria on the skin or underarm hair, a substance that releases underarm odor is produced.

The above indigenous bacteria on the skin include Staphylococcus aureus and *Propionibacterium acnes*, while the odorous components include butyric acid and valeric acid. Types of odor include underarm odor, sweat odor and hair odor.

Incidentally, general types of odor are largely classified into three types including fatty acid odor (body odor, sweat, etc.), nitrogen compound odor (decayed urine, etc.) and sulfur compound odor (excrement, etc.). Means for preventing these odors include (1) masking using fragrance, (2) adsorption using active carbons, zeolites, etc., (3) neutralization using acids and alkalis, and (4) killing of bacteria using antibacterial agents.

Masking in (1) temporarily suppresses the odor as the fragrance volatilizes, but it does not have the effect of preventing the odor from the source and the odor will come back. Adsorption in (2) presents a problem in terms of sustained effectiveness because the adsorption capacity is limited. Neutralization in (3) presents a problem in that it can be applied only for specific odors. As for killing of bacteria using antibacterial agents in (4), while some antibacterial agents trigger allergic reaction or cause irritation and are not desirable, silver-based inorganic antibacterial agents (silver zeolites) are recognized for their high safety, antibacterial spectrum, sustained effectiveness, etc., and are used in antibacterial liquids, deodorizing liquids, cosmetics, sanitary products, etc., for example.

Also, various inventions relating to silver zeolites have been proposed.

For example, a deodorizing cosmetic material is proposed that contains silicone and an antibacterial zeolite whose ion-exchangeable ions have been partially or completely ion-exchanged with metal ions such as zinc ions, ammonium ions and silver ions, and the antibacterial zeolite constituting this deodorizing cosmetic material (Zeomic AEON manufactured by Sinanen Zeomic Co., Ltd., whose average particle size is 2.5 μm) (weight of silver ions supported on silver zeolite: 2.2 percent by weight) is suggested for use in an aerosol form (refer to Patent Literature 1). There have also been attempts to suppress loss of the antibacterial action of silver ions, one example of which is a deodorizing cosmetic material offering excellent resistance to discoloration produced by blending silicone with a silver zeolite whose zeolite has been substituted by ammonium ions and silver ions (refer to Patent Literature 2).

Patent Literature 3 is known that points out that the silver zeolites mentioned above do not have immediate effect. Patent Literature 3 describes: zeolite-based antibacterial agents containing zinc, silver, copper, and other heavy metal ions are generally used as antibacterial agents against bacteria and molds, having sustained antibacterial effects for an extended period of time; among the different types of heavy metal ions, silver ions are widely used in recent years for their exceptionally high safety; and in terms of bactericidal power and deodorizing power immediately after application, silver ions demonstrate insufficient bactericidal performance compared to chlorine-based bactericides and other oxidants. To solve these problems, it proposes antibacterial agents containing silver-chloro complex salt and oxidant instead of zeolite-based antibacterial agents (refer to Patent Literature 3).

These silver zeolites mentioned above represent inventions that utilize the elution of silver ions by silver zeolite, and have a three-dimensional framework structure based on alumino-silicate, i.e., a three-dimensional framework structure of Si—O—Al—O—Si where silicon (Si) and aluminum (Al) are bonded via oxygen (O), and because aluminum (valence of +3) and silicon (valence of +4) mutually share oxygen (valence −2), the vicinity of silicon is electrically neutral, while the vicinity of aluminum has a valence of −1 (Al⁻). To compensate for this negative electric charge, normally sodium ions (Na⁻) are retained. The aforementioned silver zeolites have some of the sodium ions in their framework substituted with silver ions (Ag⁺) having antibacterial property. Their structure is such that these silver ions are electro-statically bonded in the framework and this very structure reportedly explains the excellent sustained release performance (performance of demonstrating antibacterial action over an extended period of time) of these silver zeolites as it causes the silver ions to elute as a result of ion exchange action and consequently kill bacteria.

However, the aforementioned silver zeolites need a long time to work because utilizing the elution of silver ions resulting from ion exchange with cations in the water means that bacteria are killed by silver ions that elute only gradually. In other words, it has been pointed out that they do not have immediate effect to kill bacteria quickly (refer to Non-patent Literature 1).

However, Patent Literature 4 proposes a water-based bactericide having immediate bactericidal effect, produced by using an electrolysis system. It is described that this water-based bactericide can be produced as a citric acid-silver complex from silver ions generated using an electrolysis system with silver electrodes submerged in an aqueous solution of citric acid, and from the citric acid. As shown in FIG. 6, the electrolysis system comprises a flow-rate controlled injector 40, citric acid tank 50, ion chamber 70, DC power supply 80, sedimentation tank 90, purge tank 100, and particle filter 110. An anode 71 and cathode 72 are installed in the ion chamber 70, where the anode 71 and cathode 72 are placed away from each other so that a diluted citric acid solution 62 can pass between the anode 71 and cathode 72. The anode 71 and cathode 72 are each formed from silver of 99.9999% purity. Additionally, when a sample was measured by the nuclear magnetic resonance test ($^1$H NMR) to examine the chemical structure of silver ions generated by the electrolysis system, the sample was overwhelming rich in citric acid and other anions were hardly present, which indicates compounding of complex bonds with respect to silver ions as mentioned (refer to Patent Literature 4). This suggests that it is difficult to identify the specific structure of a complex produced from silver ions and citric acid.

As mentioned above, Patent Literature 4 describes that a citric acid-silver complex can be produced using an electrolysis system having silver electrodes submerged in an aqueous solution of citric acid.

Additionally, Ciba Specialty Chemicals sells a solution containing the aforementioned citric acid-silver complex under the brand name TINOSAN SDC, and the INCI (International Nomenclature of Cosmetic Ingredients) designation of this solution is Citric Acid and Silver Citrate. It is reported that TINOSAN SDC (brand name) is an antibacterial silver for skincare use, which is a silver complex produced from silver and citric acid through a unique electrical process.

BACKGROUND ART LITERATURE

Patent Literature

[Patent Literature 1] Japanese Patent Laid-open No. Hei 08-092051
[Patent Literature 2] Japanese Patent Laid-open No. Sho 63-265809
[Patent Literature 3] PCT International Patent Laid-open No. 99/065317
[Patent Literature 4] Published Japanese Translation of PCT International Patent Application No. 2001-519361

Non-Patent Literature

Non-patent Literature 1: "Jintai Jozai Kin no Hanashi (A Story of Indigenous Bacteria in Human Body)," Noboru Aoki, Shueisha Shinsho, pp. 182-183, Dec. 20, 2009 (ninth reprint)

SUMMARY OF THE INVENTION

Problems to Be Solved by the Invention

The citric acid-silver complex described in Patent Literature 4 is produced by an electrolysis system comprising a flow-rate controlled injector 40, citric acid tank 50, ion chamber 70, DC power supply 80, sedimentation tank 90, purge tank 100, and particle filter 110, in a container that fills a diluted citric acid solution between the anode and cathode formed by high-purity silver in the ion chamber 70. Accordingly, among other costs the high equipment cost of installing the electrolysis system, and the high maintenance cost associated with the replacement of the anode and cathode formed by high-purity silver as silver consumables, make it an expensive way to produce the citric acid-silver complex, and lowering these costs is difficult. In the case of TINOSAN SDC (brand name), which is a silver complex reportedly produced by a unique electrical process, the production method used is probably similar to the method for producing a citric acid-silver complex using an electrolysis system and silver electrodes as described in Patent Literature 4.

Also, TINOSAN SDC (brand name), which is sold on the market, is recognized as an excellent antibacterial agent for skincare use because it does not contain paraben as a preservative nor alcohol, so it can be used by anyone with peace of mind as a paraben-free, alcohol-free antibacterial agent for skincare use. However, this product is not popular because it is too expensive for everyday use by general consumers. Accordingly, there is a need for a low-cost method to produce a silver-ion antibacterial liquid containing a citric acid-silver complex.

In light of the problems of the prior arts mentioned above, an object of the present invention is to provide a method for producing silver-ion antibacterial liquid that can produce at low cost a silver-ion antibacterial liquid offering immediate bactericidal effect and containing a citric acid-silver complex similar to the commercial product TINOSAN SDC (brand name), by using a silver zeolite being a low-cost material and offering characteristics that ensure high safety, as well as a silver-ion antibacterial liquid produced by such method, and a method for producing silver-ion antibacterial powder as well as a silver-ion antibacterial powder produced by such method.

Means for Solving the Problems

Existing silver zeolites are recognized for their sustained release performance through ion exchange action because Al in the three-dimensional framework of Si—O—Al—O—Si has a structure that electrically bonds with cations. For example, they are used in antibacterial liquids, deodorizing liquids, cosmetics and sanitary products, among others. Since these silver zeolites do not have immediate bactericidal effect, however, the inventor of the present invention studied repeatedly in earnest in search of a method to produce silver ions capable of killing bacteria quickly, by using any of the aforementioned silver zeolites as the material, and came up with the idea that, by collapsing the aforementioned three-dimensional framework of Si—O—Al—O—Si whose constituent silver ion ($Ag^+$) forms electrical bonds, the silver ion ($Ag^+$) could be eluted from the framework. Accordingly, a highly safe citric acid was selected for collapsing the three-dimensional framework and the citric acid was blended with a silver zeolite in purified water, and to check whether or not a citric acid-silver complex would be produced as a result of the citric acid reacting with the silver ions eluting from the framework, various experiments were conducted through trial and error and, as a result, it was discovered that, as long as the blending ratio of citric acid is 1.2 or greater relative to the blending quantity (percent by weight) of silver zeolite, then the citric acid would collapse the crystal structure forming the ion exchange site of the silver zeolite, and all silver ions contained in the silver zeolite would elute, and this discovery led to the present invention.

In other words, the method for producing silver-ion antibacterial liquid as proposed by the present invention is described below.

A method for producing silver-ion antibacterial liquid which is an invention pertaining to Embodiment 1 is a method for producing a silver-ion antibacterial liquid containing silver ions eluted from a silver zeolite, wherein the silver zeolite is a type A or type X silver zeolite, which method is characterized by comprising: a process to weigh the silver zeolite for obtaining a blending quantity of it in a range of 0.1 to 20.0 percent by weight and to weigh the citric acid for obtaining a blending quantity of it so that its blending ratio to the silver zeolite becomes 1.2 or greater, followed by blending of the silver zeolite and citric acid into purified water; a process to mix under agitation the silver zeolite and citric acid blended in the purified water to prepare a mixture liquid containing at least a citric acid-silver complex and silica hydrate; and a process to remove the silica hydrate produced in the mixture liquid.

A method for producing silver-ion antibacterial liquid which is an invention pertaining to Embodiment 2 is characterized in that the quantity of silver supported on the silver zeolite is 0.5 to 5.0 percent by weight.

A silver-ion antibacterial liquid which is an invention pertaining to Embodiment 3 is characterized in that it is produced by the method for producing silver-ion antibacterial liquid described in Embodiment 1 or 2.

A silver-ion antibacterial liquid which is an invention pertaining to Embodiment 4 is characterized in that the silver ion concentration in the silver-ion antibacterial liquid can be adjusted as desired based on the blending quantity of silver zeolite and the supported quantity of silver.

A method for producing silver-ion antibacterial powder which is an invention pertaining to Embodiment 5 is characterized in that, after the process to remove the silica hydrate under the method for producing silver-ion antibacterial liquid described in Embodiment 1, a process is added to freeze-dry or spray-dry the mixture liquid now free from silica hydrate to produce a silver-ion antibacterial powder.

A method for producing silver-ion antibacterial powder which is an invention pertaining to Embodiment 6 is characterized in that the quantity of silver supported on the silver zeolite is 0.5 to 5.0 percent by weight.

A silver-ion antibacterial powder which is an invention pertaining to Embodiment 7 is characterized in that it is produced by the method for producing silver-ion antibacterial powder described in Embodiment 5 or 6.

Effects of the Invention

The method for producing silver-ion antibacterial liquid as proposed by the present invention can significantly reduce the manufacturing cost because, instead of using the aforementioned electrolysis system and silver electrodes, it uses low-cost type A or type X silver zeolite and citric acid as materials to produce a silver-ion antibacterial liquid containing a citric acid-silver complex.

In addition, the method for producing silver-ion antibacterial liquid as proposed by the present invention involves simple process operations, partly because the blending quantity of citric acid can be easily determined as a quantity that gives a blending ratio of 1.2 or greater once the blending quantity of silver zeolite is determined, and partly because the process to produce a silver-ion antibacterial liquid comprises weighing, blending, mixing under agitation, removal of silica hydrate, and recovering a silver-ion antibacterial liquid.

The silver-ion antibacterial liquid proposed by the present invention can find widespread utilization among general users, partly because its silver ion concentration can be adjusted as desired, according to the specific application, based on the blending quantity of silver zeolite and the supported quantity of silver, and partly because it is inexpensive. Furthermore, the silver-ion antibacterial liquid can be used with peace of mind by anyone as a paraben-free, alcohol-free antibacterial agent for skincare use, for example.

In addition, the silver-ion antibacterial liquid proposed by the present invention demonstrates immediate effect to kill bacteria quickly, which was not possible through the ion exchange action of any existing silver-supporting zeolite.

The method for producing silver-ion antibacterial powder proposed by the present invention can reduce storage space by converting a silver-ion antibacterial liquid into powder form, and also allows large quantities silver-ion antibacterial to be transported because it is lighter than silver-ion antibacterial liquid.

BRIEF DESCRIPTION OF THE DRAWINGS

FIG. 1 This is an approximation straight line graph showing the correlation of the blending quantity of silver zeolite supporting 0.5 percent by weight of silver on one hand, and the silver ion concentration on the other.

FIG. 2 This is an approximation straight line graph showing the correlation of the blending quantity of silver zeolite supporting 2.5 percent by weight of silver on one hand, and the silver ion concentration on the other.

FIG. 3 This is an approximation straight line graph showing the correlation of the blending quantity of silver zeolite supporting 5.0 percent by weight of silver on one hand, and the silver ion concentration on the other.

FIG. 4 This is a graph showing the relationship of the blending quantity of silver zeolite and the silver ion concentration.

FIG. 5 This is photographs showing the properties of respective samples as observed after 1, 3, and 24 hours.

FIG. 6 This is a diagram showing the structure of a conventional electrolysis system for producing citric acid-silver complex.

MODE FOR CARRYING OUT THE INVENTION

Most Preferred Embodiment

The silver zeolite used under the present invention is either a type A or type X zeolite (any such silver zeolite is hereinafter simply referred to as "silver zeolite"). Since type X silver zeolite is expensive, preferably a type A silver zeolite is used. Type A and type X silver zeolite dissolve in acids, which is why the present invention uses these two types of zeolite. On the other hand, type Y silver zeolite and mordenite silver zeolite do not dissolve in acids and thus cannot be used. The structural formula of silver zeolite is shown below.

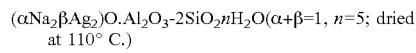

$(\alpha Na_2 \beta Ag_2)O \cdot Al_2O_3 \cdot 2SiO_2 nH_2O (\alpha+\beta=1, n=5;$ dried at 110° C.)

The crystal structure forming the ion exchange site of the above silver zeolite is a three-dimensionally bonded Si—O—Al—O—Si crystal structure whose Al has the silver ion electro-statically bonded to it, and reportedly the silver ion in the above crystal structure elutes as a result of ion exchange action to kill bacteria.

(Method for Manufacturing Silver Zeolite)

The method used to manufacture three types of silver zeolite supporting 0.5, 2.5 and 5.0 percent by weight of silver, respectively, is explained.

The explanation is based on type A zeolite as an example, but the same manufacturing procedure for type A zeolite applies when a type X zeolite is manufactured as the material. It should be noted that the method for manufacturing silver zeolite explained below is a manufacturing method normally used.

1. Silver Zeolite Supporting 0.5 Percent by Weight of Silver (1) Material
Type A zeolite (dried at 110° C.): 1000 g
Silver nitrate ($AgNO_3$): 7.9 g (2) Manufacturing Procedure Put 4.0 L of water in a 10-L plastic container and agitate. Gradually add type A zeolite (Na type) to the water to produce a suspension liquid. Agitate the liquid continuously for 3 hours or so, to release air from the solids.

Check the pH after an elapse of the specified time. Add diluted nitric acid (diluted by 6 times) by a small quantity at a time to adjust the pH to a range of 5 to 7, and use a pH litmus paper to check the pH change roughly.

Pre-mix silver nitrate with 3.0 L of water separately, and gradually introduce the mixture into the type A silver zeolite slurry under agitation. Let it stand under agitation overnight.

Install a magnetic funnel on a Nutsche, install a standard filter paper, and slowly pour the silver zeolite slurry onto the filter paper.

Before the solution runs out in the suction process, wash the filtrate with 5 L of water. Let the filtrate dry overnight at 110° C. and then cool and crush the dried filtrate into powder in a mortar. This yields a type A silver zeolite in powder state, having an average particle size of 2 to 2.5 µm.

2. Silver Zeolite Supporting 2.5 Percent by Weight of Silver (1) Material
Type A zeolite (dried at 110° C.): 1000 g
Silver nitrate ($AgNO_3$): 39.7 g (2) The Manufacturing Procedure is the Same as the One Described Above.

3. Silver Zeolite Supporting 5.0 Percent by Weight of Silver (1) Material
Type A zeolite (dried at 110° C.): 1000 g
Silver nitrate ($AgNO_3$): 79.5 g (2) The Manufacturing Procedure is the Same as the One Described Above.

(Method for Producing Silver-Ion Antibacterial Liquid)

The method for producing silver-ion antibacterial liquid as proposed by the present invention comprises: firstly, a process to weigh silver zeolite and obtain a blending quantity of it in a range of 0.1 to 20.0 percent by weight and then weigh citric acid and obtain a blending quantity of it so that its blending ratio to silver zeolite becomes 1.2 or greater, followed by blending of the two into purified water; secondly, a process to mix under agitation the silver zeolite and citric acid blended in the purified water to prepare a mixture liquid containing at least a citric acid-silver complex and silica hydrate; and finally a process to remove the silica hydrate produced in the mixture liquid; wherein, as a result of the removal process, a silver-ion antibacterial liquid is obtained that contains at least the citric acid-silver complex. The citric acid is a commercially available citric acid monohydrate. The blending ratio indicates the percentage of the blending quantity of citric acid (percent by weight) to the blending quantity of silver zeolite (percent by weight), or specifically the ratio of "Percent by weight of citric acid/Percent by weight of silver zeolite," and this ratio is defined as the "blending ratio" and used accordingly hereinafter.

The method for producing silver-ion antibacterial liquid is explained using a specific example.

(Purified Water Blending Process)

Determine the blending quantities of type A or type X silver zeolite (hereinafter referred to as "silver zeolite"), citric acid, and purified water beforehand, respectively, based on the desired quantity of silver-ion antibacterial liquid to be produced. Weigh the silver zeolite and obtain the blending quantity of it in a range of 0.1 to 20.0 percent by weight and then weigh the citric acid and obtain the blending quantity of it so that its blending ratio to the silver zeolite becomes 1.2 or greater, followed by blending of the two materials into the purified water of the pre-determined blending quantity at normal temperature (28° C.) to prepare a blended liquid. This blended liquid in which the two materials are blended together appears cloudy. Agitate the liquid to mix the materials until the cloudy liquid turns clear, to produce a mixture liquid. A clear mixture liquid should be obtained after at least 2 minutes of mixing under agitation. Or, blend the silver zeolite in the purified water at normal temperature to prepare a blended liquid, similarly blend the citric acid in the purified water at normal temperature to prepare a blended liquid, and then mix the two liquids under agitation to produce a mixture liquid. A clear mixture liquid should be obtained after at least 2 minutes of mixing under agitation. Either production method is acceptable.

Meanwhile, Zeomic AEON (manufactured by Sinanen Zeomic Co., Ltd.), a commercially available product supporting 2.2 percent by weight of silver, can also be used to produce a silver-ion antibacterial liquid in the same manner as the aforementioned production method.

(Mixture Liquid Preparation Process)

Next, the products generated by the mixture liquid preparation process are explained.

The mixture liquid prepared by blending the silver zeolite (($\alpha Na_2 \beta Ag_2$)$O \cdot Al_2O_3 \cdot 2SiO_2 nH_2O$ ($\alpha+\beta=1$, n=5; dried at 110° C.)) and citric acid ($C_6H_8O_7$) in the purified water under agitation contains a citric acid-silver complex, citric acid-aluminum complex, sodium ions ($Na^+$), and silica hydrate in light of the chemical formulas of the two materials.

As the silver zeolite and citric acid are mixed, first the proton in the citric acid ($H^+$) attacks and severs the Al—O portion in the Si—O—Al—O—Si structure of the silver zeolite, and as a result the zeolite framework collapses and the ion exchange adsorption site is lost, and this causes the silver ions to elute into the mixture liquid.

These silver ions react with the citric acid and many silver ions produce a citric acid-silver complex while a very small quantity of silver ions is produced. On the other hand, the aluminum reacts with the citric acid and produces a citric acid-aluminum complex, and in addition to the above, a silica hydrate and sodium ions are presumably produced.

The structural formula of the aforementioned citric acid-silver complex is as follows:

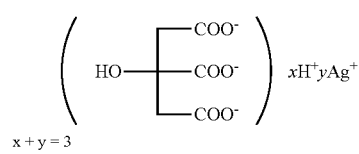

In the formula, y is 1 and/or 2, and if y is 3, the complex becomes poorly soluble and no longer dissolves in water. The citric acid-silver complex produced by the silver ion and citric acid reacting together is a complex where y is 1 and x is 2, because a majority of the complex is citrate monosilver.

(Silica Hydrate Removal Process)

An object of the present invention is to provide a method for producing silver-ion antibacterial liquid that can produce at low cost a silver-ion antibacterial liquid containing a citric acid-silver complex similar to the commercially available product TINOSAN SDC (brand name), as well as a silver-ion antibacterial liquid, etc., produced by such method. The products generated by the aforementioned mixture liquid preparation process include not only citric acid-silver complex, but also silica hydrate and citric acid-aluminum complex, among others. Aluminum citrate produced by powderizing the citric acid-aluminum complex is utilized for cosmetic applications, specifically in antiperspirants, but the silica hydrate will produce, and agglutinate as, a silica hydrate silver hydroxide when silver hydroxide is adsorbed onto its surface, and because this agglutinated product may turn into silver oxide (blackish brown color) when light is irradiated, at least the silica hydrate must be removed from the mixture liquid.

The silica hydrate can be removed by: (1) decanting the deposited agglutinated silica hydrate silver hydroxide; (2) filtering the deposited agglutinated silica hydrate silver hydroxide; (3) filtering the silica hydrate before it agglutinates; or (4) adding a divalent metal salt (such as zinc citrate) when the silver zeolite and citric acid are blended in the purified water, thereby causing the divalent metal ions to bond with the silica hydrate and deposit together, for easy removal of the silica hydrate.

(1) Removal by Decantation

Since the chemical reaction involved normally reaches an equilibrium state in 24 hours at normal temperature, by the time the mixture liquid enters an equilibrium state 24 hours after production, it has produced deposits of agglutinated silica hydrate silver hydroxide comprising the silica hydrate and silver hydroxide adsorbed onto its surface, and accordingly a silver-ion antibacterial liquid is recovered by means of decantation.

The duration of the decantation is not limited to 24 hours later, and because the silica hydrate silver hydroxide will agglutinate and deposit in the mixture liquid in 7 hours at any temperature higher than normal temperature, such as at 70° C., this indicates that a silver-ion antibacterial liquid can be recovered by means of decantation rather quickly by changing the temperature as desired.

(2) Removal by Filtering

At a normal temperature of 28° C., agglutinated silica hydrate silver hydroxide deposits in the mixture liquid in 24 hours, which means that a silver-ion antibacterial liquid can be recovered by using Watman CF/C filter paper to separate the agglutinated silica hydrate silver hydroxide, and this method provides a greater yield of silver-ion antibacterial liquid compared to the process in (1).

As mentioned above, when the temperature is raised, for example, to 70° C., agglutinated silica hydrate silver hydroxide will deposit in the mixture liquid in 7 hours, thus allowing for recovery of a silver-ion antibacterial liquid, at a better yield than under the process in (1), by means of separating the agglutinated silica hydrate silver hydroxide using the aforementioned filter paper.

(3) Removal by Filtering Before the Silica Hydrate Agglutinates

At a normal temperature of 28° C., silica hydrate will be produced in the mixture liquid in 10 minutes, so a silver-ion antibacterial liquid can be recovered by separating the silica hydrate using a filter.

(4) Removal by Causing the Zinc Citrate Ions or Calcium Citrate Ions to Bond with the Silica Hydrate and Deposit Together When the silver zeolite and citric acid are blended into the purified water, zinc citrate or calcium citrate is added to cause the zinc ions or calcium ions to bond with the silica hydrate and deposit together, after which the zinc ion- or calcium ion-bonded silica hydrate is separated by filtering to recover a silver-ion antibacterial liquid. Or, the zinc ion- or calcium ion-bonded silica hydrate can be separated by decantation to recover a silver-ion antibacterial liquid.

The process to remove silica hydrate is not limited to the processes in (1) to (4) above, and the processes in (1) to (4) above may be combined as deemed appropriate. Depending on the purpose of the silver-ion antibacterial liquid obtained according to the present invention, for example, the silver-ion antibacterial liquid recovered through the process in (3) may present problems if even a very small quantity of silica hydrate is contained, in which case a preferable way is to add the process in (4) after the process in (3) to remove silica hydrate, which effectively means that the processes in (3) and (4) can be combined to recover a silver-ion antibacterial liquid.

(Powderization of Silver-Ion Antibacterial Liquid)

Next, the method for producing silver-ion antibacterial powder involving powderization of the recovered silver-ion antibacterial liquid is explained. Following the process to remove silica hydrate under the aforementioned method for producing silver-ion antibacterial liquid, the mixture liquid now free from silica hydrate can be freeze-dried in a decompression freeze dryer or spray-dried in a decompression spray dryer to powderize the mixture liquid. For example, by using 11.0 g of silver zeolite (supporting 2.5 percent by weight of silver; dried at 110° C.) and 13.2 g of citric acid monohydrate, and treating the mixture liquid free from silica hydrate in a decompression freeze dryer, 18 g of silver-ion antibacterial powder can be produced.

When 1.0 g of the silver-ion antibacterial powder thus obtained was dissolved in 1000 g of water, the powder dissolved completely and the silver ion concentration in the obtained liquid was 15.2 ppm.

It was described that, to blend silver zeolite and citric acid for the aforementioned silver-ion antibacterial liquid, silver zeolite is weighed and a blending quantity of it in a range of 0.1 to 20.0 percent by weight is obtained, and then citric acid is weighed and a blending quantity of it is obtained so that its blending ratio to silver zeolite becomes 1.2 or greater, followed by blending of the two into purified water. The blending quantity of silver zeolite and that of citric acid were derived from the results of the first experiment described below. The first experiment was conducted in consideration of the aforementioned mechanism by which, when silver zeolite and citric acid are mixed, the proton in citric acid ($H^+$) collapses the framework structure of the Al—O portion in the Si—O—Al—O—Si structure of silver zeolite, thereby leading to loss of the ion exchange adsorption site and elution of silver ions into the mixture liquid, where it was assumed that, although a liquid in which silver zeolite is dispersed is normally cloudy, the collapse of the framework structure would turn the mixture liquid clear.

Accordingly, an experiment to examine how much citric acid should be blended relative to the blending quantity (percent by weight) of silver zeolite in order to obtain a clear mixture liquid (hereinafter referred to as the "first experiment") was conducted first. Next, an experiment to examine whether or not all silver ions supported on the silver zeolite would be eluted (hereinafter referred to as the "second experiment") was conducted, where samples with different supported quantities of silver, each representing the percent by weight of silver ions supported on silver zeolite, were used to examine the silver ion concentrations in the mixture liquids obtained as a result of the first experiment which were produced at the aforementioned blending ratio.

(First Experiment)

As examples of silver zeolite, a type A silver zeolite manufactured according to the aforementioned method for manufacturing silver zeolite, and commercially available Zeomic AJ10N (manufactured by Sinanen Zeomic Co., Ltd., supporting 2.2 percent by weight of silver), were used as samples.

Two types of the type A silver zeolite, having different blending quantities of 0.1 percent by weight and 0.5 percent by weight, respectively, were weighed and specific quantities were obtained to prepare a total of 12 samples. Also, two types of Zeomic AJ10N, also having the aforementioned different blending quantities of 0.1 percent by weight and 0.5 percent by weight, respectively, were weighed and specific quantities were obtained to prepare a total of 12 samples.

For the six samples each of the same blending quantity of 0.1 percent by weight or 0.5 percent by weight, silver zeolite was weighed and obtained at a ratio of 0.9 for Sample No. 1 and No. 7, of 1.1 for Sample No. 2 and No. 8, of 1.2 for Sample No. 3 and No. 9, of 1.3 for Sample No. 4 and No. 10, of 1.5 for Sample No. 5 and No. 11, and of 1.7 for Sample No. 6 and No. 12, as shown in the "Blending ratio" column in Table 1. Each of these weighed silver zeolites was blended with citric acid powder in purified water to prepare 200 g of blended liquid, and the pH of this mixture liquid was measured using a pH meter after 2 minutes, 10 minutes, and 30 minutes. The appearance of the mixture liquid was visually observed and characterized on a 3-point scale of cloudy, opaque, and clear.

Table 1 shows the results of the first experiment involving the total of 12 type A silver zeolite samples. The first experiment results of the total of 12 Zeomic AJ10N samples blended by 0.1 percent by weight or 0.5 percent by weight are omitted because they were shown to be identical to the first experiment results of the type A silver zeolite in Table 1 when measurement errors were considered.

It should be noted that the pH values for Nos. 1 to 12 in Table 1 were each obtained as an arithmetic mean based on a sample size of N=3. Also note that the values shown in the following tables were each obtained as an arithmetic mean based on a sample size of N=3, the same sample size applicable to the values shown in Table 1.

TABLE 1

| | Silver zeolite (supporting 2.5 w % of silver) mixed in 100 g of water | | Citric acid mixed in 100 g of water | | | Mixture liquid of silver zeolite and citric acid Observed appearance and pH (/200 g) | | | | | |
|---|---|---|---|---|---|---|---|---|---|---|---|
| | | | | | | After 2 minutes | | After 10 minutes | | After 20 minutes | |
| | Blending quantity | pH | Blending quantity | pH | Blending ratio | | | | | | |
| No. | (g) | (—) | (g) | (—) | (—) | Appearance | pH | Appearance | pH | Appearance | pH |
| 1 | 0.1 | 9.8 | 0.09 | 2.9 | 0.9 | Clouded | 4.4 | Opaque | 4.9 | Opaque | 4.9 |
| 2 | 0.1 | 9.8 | 0.11 | 2.9 | 1.1 | Clouded | 4.4 | Opaque | 4.9 | Opaque | 4.9 |
| 3 | 0.1 | 9.8 | 0.12 | 2.9 | 1.2 | Clear | 4.4 | Clear | 4.9 | Clear | 4.9 |
| 4 | 0.1 | 9.8 | 0.13 | 2.9 | 1.3 | Clear | 4.4 | Clear | 4.9 | Clear | 4.9 |
| 5 | 0.1 | 9.8 | 0.15 | 2.9 | 1.5 | Clear | 4.4 | Clear | 4.5 | Clear | 4.5 |
| 6 | 0.1 | 9.8 | 0.17 | 2.7 | 1.7 | Clear | 4.4 | Clear | 4.5 | Clear | 4.5 |
| 7 | 0.5 | 9.8 | 0.45 | 2.6 | 0.9 | Clouded | 4.4 | Opaque | 4.9 | Opaque | 4.9 |
| 8 | 0.5 | 9.8 | 0.55 | 2.5 | 1.1 | Clouded | 4.5 | Opaque | 4.8 | Opaque | 4.8 |
| 9 | 0.5 | 9.8 | 0.60 | 2.4 | 1.2 | Clear | 4.2 | Clear | 4.5 | Clear | 4.5 |
| 10 | 0.5 | 9.8 | 0.65 | 2.4 | 1.3 | Clear | 4.2 | Clear | 4.5 | Clear | 4.5 |
| 11 | 0.5 | 9.8 | 0.75 | 2.4 | 1.5 | Clear | 4.2 | Clear | 4.5 | Clear | 4.5 |
| 12 | 0.5 | 9.8 | 0.85 | 2.3 | 1.7 | Clear | 4.1 | Clear | 4.3 | Clear | 4.3 |

The results of the first experiment revealed that, with both the manufactured silver zeolite and commercially available silver zeolite, the mixture liquid remained opaque 30 minutes after mixing when the blending ratio of citric acid was 1.1 or lower relative to the blending quantity of silver zeolite, but the mixture liquid turned clear 2 minutes after mixing when the blending ratio was 1.2 or greater. Additionally, the pH reading of the clear mixture liquid was 4.0 or greater. These results of the first experiment revealed that the mixture liquid would turn clear when the blending ratio of citric acid relative to the percent by weight of silver zeolite is 1.2 or greater.

Based on the above, or specifically the fact that the mixture liquid would turn clear after 2 minutes when the blending ratio of citric acid is set to 1.2 or greater relative to the blending quantity (percent by weight) of silver zeolite, it is presumed that the citric acid collapses the crystal structure forming the ion exchange site of the silver zeolite, thereby causing the silver zeolite to elute all silver ions contained in it.

(Second Experiment)

The next example explained below pertains to the second experiment.

In the second experiment, three types of silver zeolite supporting different quantities of silver (0.5, 2.5 and 5.0 percent by weight), respectively, but all manufactured according to the aforementioned method for manufacturing silver zeolite, as well as commercially available product Zeomic AJ10N (manufactured by Sinanen Zeomic Co., Ltd., supporting 2.2 percent by weight of silver and having an average particle size of approx. 2.5 μm), were used as samples.

Then, for the aforementioned blending quantities of silver zeolite, citric acid was weighed and obtained at a blending ratio of 0.6 for Sample No. 1 to No. 3, of 0.9 for Sample No. 4 to No. 6, of 1.1 for Sample No. 7 to No. 9, of 1.2 for Sample No. 10 to No. 12, and of 1.4 for Sample No. 13 to No. 15. Then, 100 g of a blended liquid prepared by blending each weighed silver zeolite into purified water was mixed with 100 g of a blended liquid prepared by blending each weighed citric acid into purified water, to produce a mixture liquid.

Then, 200 g of the blended liquids, prepared by blending the silver zeolite and citric acid into purified water at the aforementioned blending quantities, respectively, were mixed under agitation to produce a mixture liquid. Since the chemical reaction involved normally reaches an equilibrium state in 24 hours, the silver ion concentration in the mixture liquid was measured 24 hours after its production. By the time 24 hours have elapsed, opaque deposits had been produced in the mixture liquid, so these deposits were filtered out and the obtained liquid was measured for silver ion concentration using a high-frequency inductively-coupled plasma (ICP) emission spectrometer (ICP S-8100 manufactured by Shimadzu Corporation).

In the meantime, 100 g of blended liquid of purified water and silver zeolite was mixed with 100 g of saline solution (containing 0.8 percent by weight of sodium chloride) to prepare 200 g of mixture liquid as Sample No. 16 representing a comparative example, and the concentration of eluted silver ions was measured. The concentration was 450 to 590 ppb. It should be noted that, with this comparative example No. 16, the silver ion concentration was measured by assuming the same conditions as those applicable to the spraying of silver zeolite (supporting 2.2 percent by weight of silver) for aerosol-type deodorizing cosmetic material on a sweaty body (containing 0.9 percent by weight of sodium chloride) as described in patent Literature 1.

Note that, while 100 g of a blended liquid prepared by blending each weighed silver zeolite into purified water was mixed with 100 g of a blended liquid prepared by blending each weighed citric acid into purified water, to produce a mixture liquid in the aforementioned second experiment, where the maximum blending quantity of weighed silver zeolite was 1.0 g and the maximum blending quantity of weighed citric acid was 1.3 g, this is only one example and the blending quantities are not limited to the foregoing. To permit manipulation of silver zeolite (dried at 110° C.) as a slurry, up to 50 g of silver zeolite and up to 73 g of citric acid can be blended per 100 g of purified water. The blending quantities explained above assume blending of each material separately in 100 g of purified water, but an attempt was also made to identify the maximum blending quantity of silver zeolite at which a silver-ion antibacterial liquid conforming to the present invention could be produced. Specifically, in percent by weight terms, the maximum quantity of silver zeolite was 24 percent by weight, corresponding to 28.8 percent by weight of citric acid and 47.2 percent by weight of purified water. When an attempt was made to produce a mixture liquid at these blending quantities, unreacted silver zeolite deposited and mixture liquid of dissolved silver zeolite could not be obtained. Accordingly, the experiment described below was attempted by reducing the maximum blending quantity of 24 percent by weight in order to determine the blending quantity of silver zeolite at which a silver-ion antibacterial liquid could be produced commercially, and the result revealed a preferable maximum blending quantity of silver zeolite to be 20.0 percent by weight.

Purified water was put in a 200-g flask at room temperature (28° C.), and then citric acid was introduced at each of the five different blending quantities shown in Table 2 and dissolved completely. Next, type A silver zeolite (supporting 2.5 percent by weight of silver, dried at 110° C.) was introduced under agitation at each of the five different blending quantities shown in Table 2. Then, 100 g of this mixture liquid was stored in a 100-g screw tube, and properties of the mixture liquid were observed after 1 hour, 3 hours, and 24 hours. The observed results are shown in Table 2.

TABLE 2

| No. | Blending ratio: 1.2 | | Blending quantity of silver zeolite (w %) | After 1 hour Properties | After 3 hours Properties | After 24 hours Properties |
| --- | --- | --- | --- | --- | --- | --- |
| | Silver zeolite (g) | Citric acid (g) | | | | |
| 5 | 24.0 | 28.8 | 24 | Unreacted silver zeolite had deposited. Clear. | Unreacted silver zeolite had deposited. Clear. | Gel. Blackish brown color. Unclear. |
| 1 | 20.0 | 24.0 | 20 | Fluid. Clear. | Fluid. Clear. | Gel. Blackish brown color. Unclear. |
| 2 | 15.0 | 18.0 | 15 | Fluid. Clear. | Fluid. Clear. | Gel. Blackish brown color. Unclear. |
| 3 | 10.0 | 12.0 | 10 | Fluid. Clear. | Fluid. Clear. | Fluid. Clear. |
| 4 | 5.0 | 6.0 | 5 | Fluid. Clear. | Fluid. Clear. | Fluid. Clear. |

FIG. 5 presents photographs showing the properties of respective samples as observed after 1 hour, 3 hours, and 24 hours.

Based on Table 2 and FIG. 5, silver zeolite completely dissolved and the mixture liquid was clear and fluid in Sample No. 1 to No. 4 at a blending ratio of 1.2 or greater, but silver zeolite partially deposited and did not dissolve completely in Sample No. 5. Also, in Sample No. 1 and No. 2, while the mixture liquids remained clear and fluid until 3 hours after the mixing, after 24 hours progress of agglutination of silica hydrate caused the entire system to gelate and the silica hydrate can no longer be removed by decantation or filtering. However, the silica hydrate can be removed by filtering until 3 hours after the mixing because the mixture liquid is fluid and clear. Accordingly, desirably the maximum blending quantity of silver zeolite is 20.0 percent by weight.

The results of the second experiment are shown separately for the four types of silver zeolite supporting different quantities of silver, in Table 3-1 to Table 3-4.

TABLE 3-1

Blending quantities of silver zeolite
(supporting 0.5 w % of silver) and citric acid

| No | Blending quantity silver zeolite (g) | Blending quantity of citric acid (g) | Blending ratio (—) | Silver ion concentration (ppm) |
|---|---|---|---|---|
| 1 | 0.1 | 0.06 | 0.6 | 2.0 |
| 2 | 0.5 | 0.30 | 0.6 | 10.5 |
| 3 | 1.0 | 0.60 | 0.6 | 21.5 |
| 4 | 0.1 | 0.09 | 0.9 | 2.2 |
| 5 | 0.5 | 0.45 | 0.9 | 12.8 |
| 6 | 1.0 | 0.90 | 0.9 | 25.9 |
| 7 | 0.1 | 0.11 | 1.1 | 3.4 |
| 8 | 0.5 | 0.55 | 1.1 | 14.5 |
| 9 | 1.0 | 1.10 | 1.1 | 30.5 |
| 10 | 0.1 | 0.12 | 1.2 | 3.7 |
| 11 | 0.5 | 0.60 | 1.2 | 19.3 |
| 12 | 1.0 | 1.20 | 1.2 | 38.4 |
| 13 | 0.1 | 0.14 | 1.4 | 3.8 |
| 14 | 0.5 | 0.70 | 1.4 | 18.3 |
| 15 | 1.0 | 1.40 | 1.4 | 37.4 |
| 16 | 0.5 | 0.1 (salt water) | (—) | 0.45 |

TABLE 3-2

Blending quantities of silver zeolite
(supporting 2.5 w % of silver) and citric acid

| No | Blending quantity silver zeolite (g) | Blending quantity of citric acid (g) | Blending ratio (—) | Silver ion concentration (ppm) |
|---|---|---|---|---|
| 1 | 0.1 | 0.06 | 0.6 | 10.8 |
| 2 | 0.5 | 0.30 | 0.6 | 54.8 |
| 3 | 1.0 | 0.60 | 0.6 | 102.5 |
| 4 | 0.1 | 0.09 | 0.9 | 12.3 |
| 5 | 0.5 | 0.45 | 0.9 | 60.2 |
| 6 | 1.0 | 0.90 | 0.9 | 118.7 |
| 7 | 0.1 | 0.11 | 1.1 | 16.4 |
| 8 | 0.5 | 0.55 | 1.1 | 73.8 |
| 9 | 1.0 | 1.10 | 1.1 | 152.4 |
| 10 | 0.1 | 0.12 | 1.2 | 20.4 |
| 11 | 0.5 | 0.60 | 1.2 | 93.5 |
| 12 | 1.0 | 1.20 | 1.2 | 193.8 |
| 13 | 0.1 | 0.14 | 1.4 | 18.7 |
| 14 | 0.5 | 0.70 | 1.4 | 90.5 |
| 15 | 1.0 | 1.40 | 1.4 | 185.5 |
| 16 | 2.5 | 0.1 (salt water) | (—) | 0.55 |

TABLE 3-3

Blending quantities of silver zeolite
(supporting 5.0 w % of silver) and citric acid

| No | Blending quantity silver zeolite (g) | Blending quantity of citric acid (g) | Blending ratio (—) | Silver ion concentration (ppm) |
|---|---|---|---|---|
| 1 | 0.1 | 0.06 | 0.6 | 22.1 |
| 2 | 0.5 | 0.30 | 0.6 | 105.4 |
| 3 | 1.0 | 0.60 | 0.6 | 215.5 |
| 4 | 0.1 | 0.09 | 0.9 | 26.7 |
| 5 | 0.5 | 0.45 | 0.9 | 122.3 |
| 6 | 1.0 | 0.90 | 0.9 | 244.4 |
| 7 | 0.1 | 0.11 | 1.1 | 29.1 |
| 8 | 0.5 | 0.55 | 1.1 | 148.0 |
| 9 | 1.0 | 1.10 | 1.1 | 293.7 |
| 10 | 0.1 | 0.12 | 1.2 | 36.9 |
| 11 | 0.5 | 0.60 | 1.2 | 180.4 |
| 12 | 1.0 | 1.20 | 1.2 | 377.4 |
| 13 | 0.1 | 0.14 | 1.4 | 44.3 |
| 14 | 0.5 | 0.70 | 1.4 | 191.5 |
| 15 | 1.0 | 1.40 | 1.4 | 386.7 |
| 16 | 5.0 | 0.1 (salt water) | (—) | 0.59 |

TABLE 3-4

Blending quantities of Zeomic AJ01N
(supporting 2.2 w % of silver) and citric acid

| No | Blending quantity silver zeolite (g) | Blending quantity of citric acid (g) | Blending ratio (—) | Silver ion concentration (ppm) |
|---|---|---|---|---|
| 1 | 0.1 | 0.06 | 0.6 | 13.1 |
| 2 | 0.5 | 0.30 | 0.6 | 65.2 |
| 3 | 1.0 | 0.60 | 0.6 | 125.9 |
| 4 | 0.1 | 0.09 | 0.9 | 15.8 |
| 5 | 0.5 | 0.45 | 0.9 | 77.5 |
| 6 | 1.0 | 0.90 | 0.9 | 152.5 |
| 7 | 0.1 | 0.11 | 1.1 | 20.1 |
| 8 | 0.5 | 0.55 | 1.1 | 95.3 |
| 9 | 1.0 | 1.10 | 1.1 | 187.7 |
| 10 | 0.1 | 0.12 | 1.2 | 20.7 |
| 11 | 0.5 | 0.60 | 1.2 | 100.3 |
| 12 | 1.0 | 1.20 | 1.2 | 198.6 |
| 13 | 0.1 | 0.14 | 1.4 | 20.8 |
| 14 | 0.5 | 0.70 | 1.4 | 98.1 |
| 15 | 1.0 | 1.40 | 1.4 | 201.9 |
| 16 | 2.5 | 0.1 (salt water) | (—) | 0.56 |

With regard to the silver ion concentrations in Table 3-1 to Table 3-4, the comparative example No. 16 has concentrations ranging from 0.45 to 0.59 ppm and it is clear that at these values antibacterial effect is demonstrated. Examples No. 1 to No. 15 have a minimum silver ion concentration of 2.0 ppm, which corresponds to approx. four times the concentration of the comparative example and it is clear that antibacterial effect is demonstrated.

Next, a graph of eluted silver ion concentration plotting three different blending quantities of silver zeolite (0.1, 0.5, and 1.0 percent by weight) along the horizontal axis and plotting three different silver ion concentrations corresponding to these values along the vertical axis, was created for each of five different blending ratios based on Table 3-1 to Table 3-3 showing the second experiment results of three types of silver zeolite supporting different quantities of silver. FIG. 1 is an approximation straight line graph showing the correlation of the blending quantity of silver zeolite supporting 0.5 percent by weight of silver on one hand, and the silver ion concentration on the other. FIG. 2 is an approximation straight line graph showing the correlation of the blending quantity of silver zeolite supporting 2.5 percent by weight of silver on one hand, and the silver ion concentration on the other. FIG. 3 is an approximation straight line graph showing the correlation of the blending quantity of silver zeolite supporting 5.0 percent by weight of silver on one hand, and the silver ion concentration on the other. Approximation straight lines for Sample No. 13 to No. 15 are denoted by the symbol ●, approximation straight lines for Sample No. 10 to No. 12 are denoted by the symbol ▲, approximation straight lines for Sample No. 7 to No. 9 are denoted by the symbol Δ, approximation straight lines for Sample No. 4 to No. 6 are denoted by the symbol ○, and approximation straight lines for Sample No. 1 to No. 3 are denoted by the symbol ◊.

From the graphs in FIG. 1 to FIG. 3, the silver ion concentrations at blending ratios of 1.1 and lower are far lower than the silver ion concentrations at blending ratios of 1.2 and greater. Additionally, it is clear that the graphs of Sample No. 13 to No. 15 denoted by the symbol ● and graphs of Sample No. 10 to No. 12 denoted by the symbol ▲, all representing a blending ratio of 1.2 or greater, have roughly identical silver ion concentrations when measurement errors are taken into consideration, which is not the case with the graphs of other samples denoted by the symbols Δ, ○ and ◇. It should be noted that the approximation straight lines for the samples of Zeomic AJ10N (manufactured by Sinanen Zeomic Co., Ltd.) in Table 3-4 are omitted because these lines closely follow the approximation straight lines for the samples of silver zeolite supporting 2.5 percent by weight of silver and the latter lines can be used instead.

Samples 1 to 15 in the second experiment are examples where the maximum blending quantity of weighed silver zeolite is 1.0 g and the maximum blending quantity of weighed citric acid is 1.3 g, and one of these samples, No. 15 in Table 3-3, represents a silver ion concentration of 386.7 ppm with 5.0 percent by weight of silver supported. However, it is indicated that this silver ion concentration, while peaking in No. 15 among the samples, can be raised by increasing the blending quantity of silver zeolite and supported quantity of silver so long as the blending ratio is 1.2 or greater. According to the purpose of the produced silver-ion antibacterial liquid, its silver ion concentration can be adjusted as desired based on the blending quantity of silver zeolite and supported quantity of silver.

In the meantime, while it was mentioned based on the first experiment that all silver ions supported on the silver zeolite could be presumably eluted as long as citric acid is introduced into purified water by a blending quantity that gives a blending ratio of 1.2 or greater relative to the blending quantity of silver zeolite, the fact that Sample No. 10 to No. 12 denoted by the symbol ▲ have a blending ratio of 1.2 and Sample No. 13 to No. 15 denoted by the symbol ● have a blending ratio of 1.4 indicates that Samples No. 10 to No. 12 and No. 13 to No. 15 have roughly identical silver ion concentrations when measurement errors are taken into consideration because all silver ions supported on the silver zeolite were eluted.

Accordingly, Table 4 was created by extracting only the data of blending quantity of silver zeolite and silver ion concentration pertaining to No. 10 to No. 12 and No. 13 to No. 15 in Table 3-1 to Table 3-3. Then, FIG. 4, representing the relationship of blending quantity of silver zeolite and silver ion concentration, was created based on this data of Table 4.

TABLE 4

| No | Blending quantities of silver zeolite supporting 0.5 w % of silver | Blending quantities of silver zeolite supporting 2.5 w % of silver | Blending quantities of silver zeolite supporting 5.0 w % of silver |
|---|---|---|---|
| 10 | 3.7 | 20.4 | 36.9 |
| 11 | 19.3 | 93.5 | 180.4 |
| 12 | 38.4 | 193.8 | 377.4 |
| 13 | 3.8 | 18.7 | 44.3 |
| 14 | 18.3 | 90.5 | 191.5 |
| 15 | 37.4 | 185.5 | 386.7 |

FIG. 4 is a graph showing the relationship of blending quantity of silver zeolite and silver ion concentration, created by plotting three different blending quantities of silver zeolite (0.1, 0.5, and 1.0 g) along the horizontal axis and plotting the corresponding silver ion concentrations along the vertical axis. The symbol ◇ represents an approximation straight line for Sample No. 10 (y=36.73x+0.7443), while the symbol x represents an approximation straight line for Sample No. 13 (y=45.243x−1.8598), and the supported quantity of silver is 0.5 percent by weight for Sample No. 10 and No. 13. The symbol □ represents an approximation straight line for Sample No. 11 (y=178.79x+2.3803), while the symbol * represents an approximation straight line for Sample No. 14 (y=192.84x−2.7459), and the supported quantity of silver is 2.5 percent by weight for Sample No. 11 and No. 14. The symbol Δ represents an approximation straight line for Sample No. 12 (y=376.28x+0.518), while the symbol ○ represents an approximation straight line for Sample No. 15 (y=388.49x−3.1623), and the supported quantity of silver is 5.0 percent by weight for Sample No. 12 and No. 15.

FIG. 4 shows that, when errors are taken into consideration, the approximation straight lines of Sample No. 10 and No. 13 (supported quantity of silver=0.5 percent by weight) are identical, while the approximation straight lines of Sample No. 11 and No. 14 (supported quantity of silver=2.5 percent by weight) are also identical, and the approximation straight lines of Sample No. 12 and No. 15 (supported quantity of silver=5.0 percent by weight) are yet also identical. The foregoing indicates that, even when the supported quantity of silver varies from 0.5 percent by weight to 2.5 percent by weight or to 5.0 percent by weight, all silver ions supported on the silver zeolite can be eluted as long as citric acid is blended into purified water by a blending quantity (percent by weight) that gives a blending ratio of 1.2 or greater relative to the blending quantity of silver zeolite (percent by weight).

An object of the present invention is to provide a method for producing silver-ion antibacterial liquid that can produce at low cost a silver-ion antibacterial liquid containing a citric acid-silver complex, by using a silver zeolite being a low-cost material and offering characteristics that ensure high safety, etc. The commercial product TINOSAN SDC (brand name) is recognized as an excellent antibacterial agent as it contains a citric acid-silver complex and can be used safely as a paraben-free, alcohol-free antibacterial agent for skincare use. However, the TINOSAN SDC (brand name) is too expensive for everyday use by general consumers and thus is not popular. If a silver-ion antibacterial liquid containing a citric acid-silver complex can be produced from silver zeolite, then cosmetic liquids, etc., in a popular price range can be produced.

(NMR Spectral Analysis)

Accordingly, produced silver-ion antibacterial liquid was powderized and put through NMR (nuclear magnetic resonance) spectral analysis.

Example

In Example 1, 1 g of type A silver zeolite supporting 2.5 percent by weight of silver was blended in purified water with 1.2 g of citric acid at a blending ratio of 1.2, to prepare 100 g of aqueous solution, and then the aqueous solution was agitated for 2 hours at normal temperature and then treated at 80° C. for 1 hour to cause the silica component to agglutinate, after which the solution was kept stationary for 2 days to let the agglutinated silica component deposit, and the filtrate was turned into powder (18.8 mg of silver/1.2 g) using a decompression freeze dryer to obtain a sample.

Comparative Examples

In Comparative Example 1, TINOSAN SDC was turned into powder using a freeze dryer to obtain a sample.

In Comparative Example 2, citric acid, being the reagent, was used as a sample.

Then, 10 mg of each sample was dissolved in 0.8 g of heavy water and put through 600 MHz H-NMR (nuclear magnetic resonance) spectral analysis.

Citric acid-silver complex signals could not be identified from the spectral signals of the Example and Comparative Examples 1 and 2.

Because NMR failed to identify a citric acid-silver complex, as the next step the chemical reaction of silver zeolite and citric acid was examined and the products contained in the produced mixture liquid were examined.

(Products Contained in Mixture Liquid)

As mentioned earlier, the structural formula of silver zeolite is as follows:

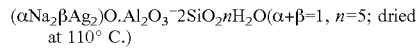

($\alpha Na_2 \beta Ag_2$)$O \cdot Al_2O_3 \cdot 2SiO_2 \cdot nH_2O$ ($\alpha+\beta=1$, $n=5$; dried at 110° C.)

The crystal structure forming the ion exchange site of the silver zeolite is such that the silver ion is electro-statically bonded to the Al portion in the three-dimensionally bonded Si—O—Al—O—Si crystal structure, and reportedly the silver ion in the above crystal structure elutes as a result of ion exchange action to kill bacteria. In other words, the structure of type A silver zeolite is that of aluminosilicate comprising silica ($SiO_2$) and alumina ($Al_2O_3$), whose framework is characterized by a crystal structure based on three-dimensionally bonded $(AlO_4)^-$ tetrahedral and $(SiO_4)^-$ tetrahedral, with the silver ion electro-statically adsorbed to the Al portion.

The process of how type A silver zeolite is collapsed by citric acid is considered as follows:

1. The proton of citric acid undergoes ion exchange with the sodium ion present at the negatively charged position on the $(AlO_4)^-$ tetrahedral of type A silver zeolite (because the selectivity coefficient of the sodium ion is smaller than that of the silver ion).

2. The excess proton acts upon and severs the Al—O bond in the framework.

3. The severance of the Al—O bond causes the framework structure to collapse, and the silver ions, sodium ions, etc., that have been adsorbed onto the silver zeolite are released into the solution.

4. The released silver ions react with the citric acid to produce a citric acid-silver complex.

5. The aluminum reacts with $C_6H_5O_7^{3-}$ of citric acid to produce a citric acid-aluminum complex.

6. The citric acid-silver complex partially dissociates in water, causing a very small quantity of silver ions to be also present in water.

7. Sodium is present as ions in water.

8. Silicon is suspended or deposited as silica gel. The suspended/deposited silica gel has a small quantity of silver ions adsorbed onto its surface.

In consideration of the aforementioned chemical reaction, the products contained in the mixture liquid likely include citric acid-silver complex, silica hydrate, citric acid-aluminum complex, and silver ions.

Accordingly, silica hydrate has been naturally removed from the silver-ion antibacterial liquid produced by the method for producing silver-ion antibacterial liquid as proposed by the present invention.

It is significant that the method for producing silver-ion antibacterial liquid as proposed by the present invention illuminates the bonding ratio of citric acid with respect to silver zeolite as 1.2 or greater. This means that, whenever a silver-ion antibacterial liquid containing a citric acid-silver complex is to be prepared, optimal manufacturing conditions and economy would be achieved by blending citric acid at a blending ratio of 1.2 or greater with respect to silver zeolite.

What is claimed is:

1. A method for producing silver-ion antibacterial liquid containing silver ions fully eluted from silver zeolite, by collapsing a three-dimensional framework of the silver zeolite using citric acid, said silver-ion antibacterial liquid being obtained by mixing solely a material consisting of the silver zeolite, citric acid, and purified water, said method comprising:

a process to weigh the silver zeolite wherein the silver zeolite is a type A silver zeolite for obtaining a blending quantity of the silver zeolite such as to be in a range of 0.1 to 20.0 percent by weight relative to the weight of the material, and to weigh citric acid for obtaining a blending quantity of the citric acid in a range of 0.12 to 28.0 percent by weight relative to the weight of the material such that a blending weight ratio of the citric acid to the silver zeolite becomes 1.2 or greater but 1.4 or less, followed by blending the silver zeolite and the citric acid into the purified water;

a process to mix under agitation the silver zeolite and citric acid blended in the purified water, thereby collapsing the three-dimensional framework of the silver zeolite, to prepare a mixture liquid containing a citric acid-silver complex

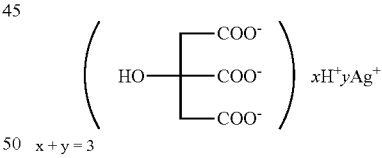

$x+y=3$ wherein y is 1 or 2, and silica hydrate; and a process to remove the silica hydrate produced in the mixture liquid.

2. A method for producing silver-ion antibacterial liquid according to claim 1, wherein the silver zeolite contains silver supported thereon in an amount of 0.5 to 5.0 percent by weight relative to the silver zeolite.

* * * * *